(12) United States Patent
Shi et al.

(10) Patent No.: US 10,280,153 B2
(45) Date of Patent: May 7, 2019

(54) PROCESS FOR THE PREPARATION OF PURE NILOTINIB AND ITS SALT

(71) Applicant: F.I.S.—Fabbrica Italiana Sintetici S.p.A., Montecchio Maggiore (IT)

(72) Inventors: JinPu Shi, Ningbo Zhejiang (CN); Roberto Profeta, Occhiobello (IT)

(73) Assignee: F.I.S.—Fabbrica Italiana Sintetici S.p.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/979,849

(22) Filed: May 15, 2018

(65) Prior Publication Data

US 2018/0334449 A1     Nov. 22, 2018

(30) Foreign Application Priority Data

May 16, 2017   (EP) ..................................... 17171267

(51) Int. Cl.
  *C07D 401/14*     (2006.01)
  *C07D 233/61*     (2006.01)
(52) U.S. Cl.
  CPC .......... *C07D 401/14* (2013.01); *C07D 233/61* (2013.01); *C07B 2200/13* (2013.01)
(58) Field of Classification Search
  CPC ... C07D 233/61; C07D 401/14; A61K 31/506

USPC ........................................... 544/331; 514/275
  See application file for complete search history.

(56) References Cited

U.S. PATENT DOCUMENTS

| 7,169,791 | B2 | 1/2007 | Breitenstein et al. |
| 8,163,904 | B2 | 4/2012 | Manley et al. |
| 2013/0210847 | A1 | 8/2013 | Kompella et al. |

FOREIGN PATENT DOCUMENTS

| WO | WO 2007/015870 A2 | 7/2005 | |
| WO | WO 2010/009402 A2 | 1/2010 | |
| WO | WO 2010/054056 A2 | 5/2010 | |
| WO | WO 2011/033307 A1 | 3/2011 | |
| WO | WO 2011/086541 A1 | 7/2011 | |
| WO | WO-2011086541 A1 * | 7/2011 | ........... C07D 401/14 |
| WO | WO 2011/163222 A1 | 12/2011 | |
| WO | WO 2012/070062 A2 | 5/2012 | |
| WO | WO-2014174456 A2 * | 10/2014 | ........... C07D 401/14 |
| WO | WO 2015/087343 A2 | 6/2015 | |
| WO | WO-2016024289 A2 * | 2/2016 | ........... C07D 401/14 |
| WO | WO 2016/151304 A1 | 9/2016 | |
| WO | WO-2016151304 A1 * | 9/2016 | ........... C07D 401/14 |

* cited by examiner

*Primary Examiner* — Venkataraman Balasubramanian
(74) *Attorney, Agent, or Firm* — Sterne, Kessler, Goldstein Fox

(57) ABSTRACT

Object of the present invention is a process for the preparation of the pharmaceutical active ingredient Nilotinib free base or Nilotinib dihydrochloride dihydrate by means of an improved crystallization procedure.

16 Claims, No Drawings

PROCESS FOR THE PREPARATION OF PURE NILOTINIB AND ITS SALT

This Patent Application claims priority to and benefit of EP Application No. EP17171267.2 filed on May 16, 2017, the content of which are incorporated herein by reference in its entirety.

TECHNICAL FIELD

The present invention refers to a process for the preparation of pure Nilotinib and its salt.

BACKGROUND ART

The drug compound having the adopted name Nilotinib has chemical name 4-methyl-N-[3-(4-methyl-1H-imidazol-1-yl)-5-(trifluoromethyl)phenyl]-3-[[4-(3-pyridinyl)-2-pyrimidinyl]amino]-benzamide, and is structurally represented by formula (I):

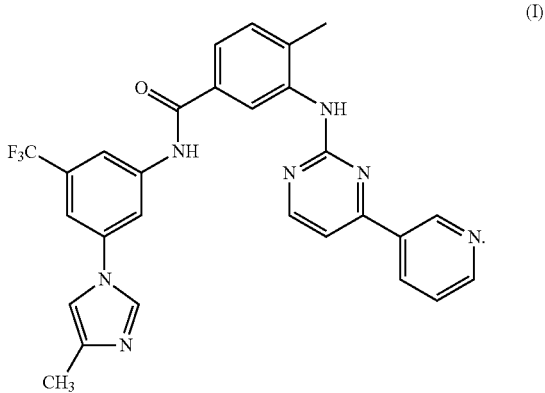 [SMILES: Cc1cn(-c2cc(NC(=O)c3ccc(C)c(Nc4nccc(-c5cccnc5)n4)c3)cc(C(F)(F)F)c2)cn1]

Nilotinib is a small-molecule tyrosine kinase inhibitor approved for the treatment of imatinib-resistant chronic myelogenous leukemia. Structurally related to Imatinib, it was developed based on the structure of the Abl-imatinib complex to address Imatinib intolerance and resistance.

Nilotinib is a selective Bcr-Abl kinase inhibitor that is 10-30 fold more potent than Imatinib. It has been available in the market in Europe since September 2009 as mono-hydrochloride mono-hydrate salt, form B under the tradename Tasigna®.

U.S. patent application Ser. No. 10/520,359 discloses Nilotinib and process for its preparation. The disclosed process involves the reaction of ethyl-3-amino-4-methylbenzoate (1) with cyanamide in presence of hydrochloric acid in ethanol followed by treatment with aqueous ammonium nitrate to provide 3-[(aminoiminomethyl)amino]-4-methyl-benzoic acid ethylester mononitrate (2); this intermediate, on further treatment with 3-(dimethylamino)-1-(pyridine-3-yl)prop-2-en-1-one (3) in presence of sodium hydroxide in ethanol, provides 4-methyl-3-{[4-(3-pyridinyl)-2-pyrimidinyl]amino}benzoic acid ethylester (4); said ethyl ester compound (4) was hydrolyzed using sodium hydroxide in ethanol solvent; the obtained 4-methyl-3-{[4-(3-pyridinyl)-2-pyrimidinyl]amino}benzoic acid (5) is coupled with 5-trifluoromethyl-3-[4-methyl-1H-imidazolyl] aniline (6) in the presence of diethylcyanophosphate and a base (triethylamine) in dimethylformamide to provide Nilotinib. The said process is represented in the following scheme:

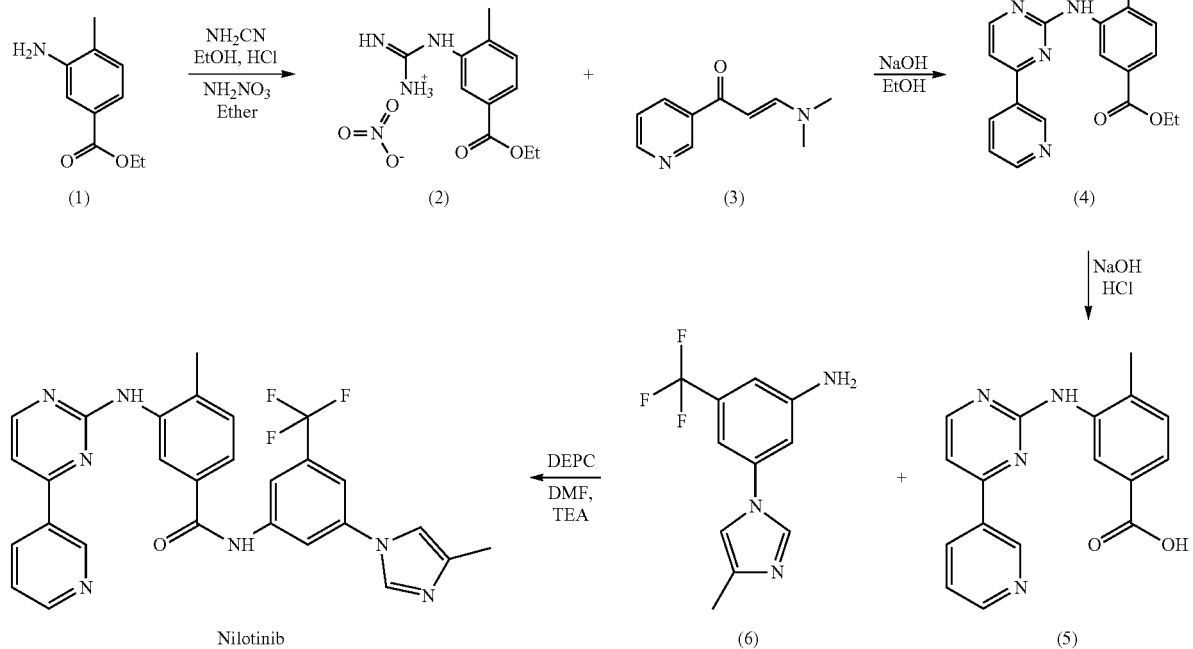

A particularly useful salt of Nilotinib is Nilotinib hydrochloride monohydrate as disclosed in U.S. patent application Ser. No. 11/995,898. This application discloses two polymorphic forms of Nilotinib hydrochloride monohydrate, namely "Form A" and "Form B". Said application also discloses various other salts of Nilotinib, namely monophosphate, diphosphate, sulfate, mesylate, esylate, besylate and tosylate and processes for their preparation. Example 1 of U.S. patent application Ser. No. 11/995,898 describes a process for preparing Nilotinib hydrochloride monohydrate, whose the resulting product is characterized by an X-Ray diffraction (XPRD) pattern having peaks at 7.4, 9.4, 11.6, 12.1. 15.8, 19.3, 22.1, 24.1 and 25.7±0.2 degrees 2-theta. Form B is described in U.S. patent application Ser. No. 11/995,898 as being hygroscopic and very poorly soluble in water.

International application publication No. WO 2007/015870 A2 describes substantially pure crystalline forms of Nilotinib hydrochloride designated as Form A, Form A', Form A", Form B, Form B', Form Ss, Form Ss', Form C, Form C', Form Se, Form D, Form SE, mixture of Form B and Form D, and amorphous form of Nilotinib hydrochloride. Further, it also discloses substantially pure crystalline forms A and B of Nilotinib free base and substantially pure crystalline forms A and B of Nilotinib sulfate salt.

International application publication No. WO 2010/009402 discloses a process which involves the reaction of 4-methyl-3-{[4-(pyridin-3-yl)pyrimidin-2-yl]amino}benzoic acid with 5-trifluoromethyl-3-[4-methyl-1H-imidazolyl]aniline in the presence of thionyl chloride in N-methylpyrrolidine solvent to provide Nilotinib.

International application publication No. WO 2010/054056 A2 describes polymorphic forms of Nilotinib hydrochloride designated as forms T1, T2, T3, T4, T5, T6, T7, T8, T9, T10, T11, T12, T13, T14, T15 T16, T17, T18, and T19. Further, it also describes solid dispersion of Nilotinib hydrochloride in combination with a pharmaceutically suitable excipient.

International application publication No. WO 2011/163222 describes polymorphic forms of Nilotinib hydrochloride designated as forms T20, T27, T28 and T29.

International application publication No. WO 2011/086541 A1 describes a crystalline form of Nilotinib hydrochloride monohydrate having an X-ray diffraction pattern comprising peaks at 5.70, 7.56, 9.82, 15.01, 17.31 and 27.68±0.2 degrees 2-theta and process for its preparation.

International application publication No. WO 2012/070062 A2 describes Nilotinib hydrochloride crystalline form H1, characterized by peaks in the powder x-ray diffraction spectrum having 2-theta angle positions at about 8.6, 11.4, 13.2, 14.3, 15.5, 17.3, 19.2 and 25.3±0.2 degrees and a process for its preparation.

US application publication No. 2013/0210847 A1 describes Nilotinib hydrochloride dihydrate, characterized by peaks in the powder X-ray diffraction pattern at 4.3, 8.7, 9.5, 11.3, 13.2, 14.4, 17.3, 18.6, 19.3, 20.8, 22.2 and 25.3 degrees 2-theta (±0.1 degrees 2-theta).

International application publication No. WO 2011/033307 discloses Nilotinib dihydrochloride and its hydrates, in particular Nilotinib dihydrochloride dihydrate characterized by XPRD, Differential Scanning calorimetry (DSC) and Thermogravimetric analysis (TGA). Also disclosed is a process for the preparation thereof and pharmaceutical compositions containing these compounds as well as the use of the compounds in the treatment of cancer.

Nilotinib dihydrochloride dihydrate disclosed in WO 2011/033307 is characterized by (i) an XPRD pattern comprising peaks at 7.18, 14.32, 23.34 and 27.62±0.2 degrees; and (ii) a DSC thermogram with endothermic peaks at about 107±2° C. and 251±2° C.

International application publication No. WO 2015/087343 discloses, in the Example 4, a process for the preparation of Nilotinib. The disclosed process involves a coupling reaction of 4-methyl-3-{[4-(3-pyridinyl)-2-pyrimidinyl]amino}benzoic acid (5) with 5-trifluoromethyl-3-[4-methyl-1H-imidazolyl]aniline (6) in presence of carbonyl diimidazole and imidazole hydrochloride in N-methylpyrrolidine as a solvent. After completion of the coupling reaction, the reaction mass was cooled and a sodium hydroxide solution was added. The disclosed process provides Nilotinib free base in 52.63% molar yield and has a purity of 99.84% by HPLC, containing 0.03% of 4-methyl-3-{[4-(3-pyridinyl)-2-pyrimidinyl]amino}benzoic acid (also name as acid impurity).

International application publication No. WO 2016/1513304 discloses, in example 1, a process for the preparation of Nilotinib dihydrochloride dihydrate. The disclosed process involves a coupling reaction of 4-methyl-3-{[4-(3-pyridinyl)-2-pyrimidinyl]amino}benzoic acid (5) with 5-trifluoromethyl-3-[4-methyl-1H-imidazolyl]aniline (6) in presence of thionyl chloride in N-methylpyrrolidone as a solvent. After completion of the coupling reaction, the reaction mass was cooled and water and acetone was added. The disclosed process provides Nilotinib free base. The Nilotinib free base was dissolved in a mixture of conc. HCl and methanol, being then filtered through hyflo. The obtained solution was concentrated to residue and the residue was dissolved in a mixture of water an methanol. The obtained solution was slowly added to the acetonitrile and thus obtaining a suspension of the product which was filtered to obtain the solid of title compound. The disclosed process provides thus Nilotinib dihydrochloride dihydrate in 67.27% molar yield, which is quite a low value of yield.

SUMMARY OF INVENTION

The problem addressed by the present invention is therefore that of providing an improved process for the preparation of 4-methyl-N-[3-(4-methyl-1H-imidazol-1-yl)-5-(trifluoromethyl)phenyl]-3-[[4-(3-pyridinyl)-2-pyrimidinyl]amino]benzamide and a salt thereof which allows to get round to the drawbacks above reported with reference to the known prior art.

In particular, the process of the invention solves this problem providing a process which provides Nilotinib base having a low amount of impurity acid and, at the same time, with higher molar yield, if compared with the known processes.

This problem is solved by a process for the preparation of a said compound, which also is a key intermediate for the synthesis of compounds having anti-tumor activity, as outlined in the annexed claims, whose definitions are integral part of the present description.

Further features and advantages of the process according to the invention will result from the description hereafter reported of examples of realization of the invention, provided as an indication and not as a limitation of the invention.

DETAILED DESCRIPTION OF THE INVENTION

The present invention relates to the preparation of Nilotinib free base of formula (I):

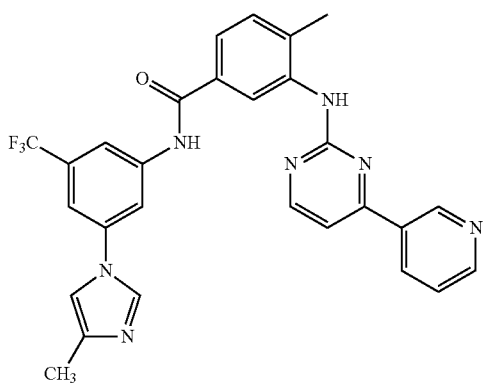

with improved purity and higher molar yield if compared to the known processes. In particular, the invention relates to a process of purification of Nilotinib free base.

Moreover, another object of the present invention is the preparation of the Nilotinib salt named Nilotinib dihydrochloride dihydrate from the purified Nilotinib free base.

Nilotinib free base raw material can be obtained by any of the processes known from the prior art, e.g. as described in WO 2015/087343 example 4 or in WO 2016/1513304 example 1 first part.

The process of the invention comprises the following steps:
(a) providing a solution of the compound of formula (I) free base raw material:

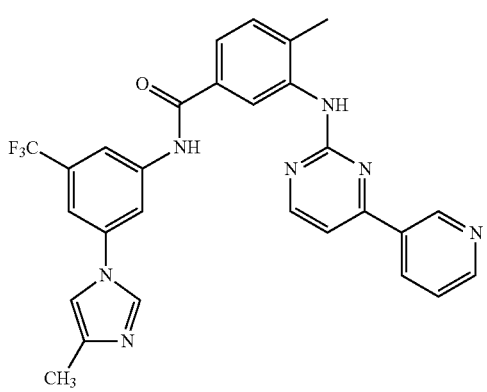

in a mixture of $C_1$-$C_4$ alcohol and a mineral acid;
(b) adding a base to the solution of the step (a) to achieve a value of pH more than 8;
(c) optionally, seeding the solution of step (b);
(d) obtaining a suspension of the compound of formula (I);
(e) isolating the product of formula (I).

It has been found that this recrystallization step is of pivotal importance in order to reduce to a very low threshold the impurities generated in the previous steps of the synthesis of Nilotinib free base. In fact, the subsequent step of salification of Nilotinib is not able to improve the purity of the product.

In particular, if Nilotinib free base has been prepared by a coupling reaction of 4-methyl-3-{[4-(3-pyridinyl)-2-pyrimidinyl]amino}benzoic acid (5) with 5-trifluoromethyl-3-[4-methyl-1H-imidazolyl]aniline (6), these two starting materials constitute the main impurities that the inventive process is able to minimize. Even if the elimination of such impurities is a preferred aspect of the invention, it should be understood however that the purification process of the invention can be applied to any other Nilotinib free base raw material irrespective of the synthesis process which has been subjected to.

In preferred embodiments, the step (a) comprises the following steps:
(a-1) provide the compound of formula (I) as a solid:

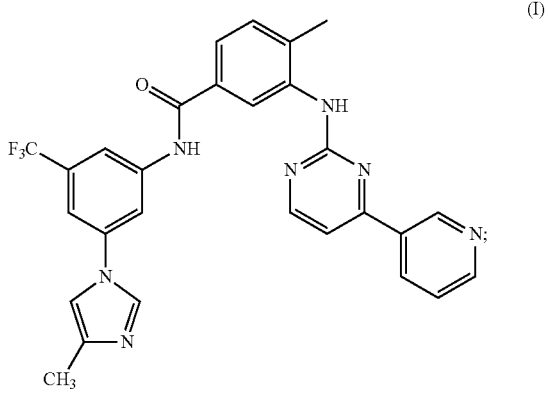 [SMILES: Cc1cn(-c2cc(NC(=O)c3ccc(C)c(Nc4nccc(-c5cccnc5)n4)c3)cc(C(F)(F)F)c2)cn1]

(a-2) dissolving said solid in a mixture of $C_1$-$C_4$ alcohol and a mineral acid.

The step (a-2) can be carried out in various way, e.g. by:
(a-2-1) suspending the compound of formula (I) in $C_1$-$C_4$ alcohol and then adding a mineral acid; or by:
(a-2-2) adding a mixture of $C_1$-$C_4$ alcohol and a mineral acid to a solid compound of formula (I).

Alternatively, the step (a) can be carried out by preparing Nilotinib and obtaining it in a $C_1$-$C_4$ alcohol.

Alternatively, the step (a) can be carried out by preparing Nilotinib and obtaining it in a mixture of a mixture of $C_1$-$C_4$ alcohol and a mineral acid.

The term of linear or branched $C_1$-$C_4$ alcohol thus means an alcohol selected among: methanol, ethanol, n-propanol, isopropanol, n-butanol, isobutanol, sec-butanol and tert-butanol.

According to preferred embodiment, the linear or branched $C_1$-$C_4$ alcohol is methanol.

According to a preferred embodiment, the step (a) of the process according to the invention can be carried out using from 5 to 25 volumes (V) of $C_1$-$C_4$ alcohol, preferably comprises from 10 to 20 volumes (V).

In certain embodiments, an amount of between 10 and 20 volumes of $C_1$-$C_4$ alcohol is used. Preferably, from 13 to 17 volumes of $C_1$-$C_4$ alcohol are used as a solvent.

According to a preferred embodiment, the step (a) of the process according to the invention can be carried out using from 5 to 25 volumes (V) of methanol, preferably comprises from 10 to 20 volumes (V).

In certain embodiments, an amount of between 10 and 20 volumes of methanol is used. Preferably, from 13 to 17 volumes of methanol are used as a solvent.

The term "volume" means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

Thus, for example, if 1 g of Nilotinib free base is to be purified, it will be suspended preferably in 13 to 17 ml of methanol.

The term a mineral acid thus means an mineral acid selected among: hydrochloric acid, hydrobromic acid, hydroiodic acid, sulfuric acid, nitric acid.

In a preferred embodiment, the mineral acid is an aqueous mineral acid, more preferably is aqueous hydrochloric acid.

It has been surprisingly found that while Nilotinib free base is poorly soluble in methanol, the presence of the mineral acid solubilises it.

In preferred embodiments, the pH in the Nilotinib solution of step (a) is comprised between 2 and 4. More preferably, the pH is comprised between 2.3 and 3.2.

Only a slight excess of mineral acid is sufficient. In certain embodiments, about 1.02 equivalents of mineral acid, e.g. methanol, are used to achieve the best conditions of treatment.

In preferred embodiments, step (a) is conducted at a temperature between 50° C. and 80° C. More preferably, the temperature in step (a) is comprised between 55° C. and 65° C. At this temperature a substantially clear solution is achieved.

The term "substantially clear solution" is to be understood as a solution wherein some particulate material may be present. For example, if Nilotinib free base is prepared from 4-methyl-3-{[4-(3-pyridinyl)-2-pyrimidinyl]amino}benzoic acid (5) and 5-trifluoromethyl-3-[4-methyl-1H-imidazolyl] aniline (6), some particulate of the highly insoluble intermediate (5) may be present. Also inorganic particles may be present in the solution.

If particulate material is present in the solution, this can optionally be filtered on a carbon filter. This operation has the additional advantage of discolouring the solution, that from an orange/red colour changes into a yellow/yellowish solution.

The solution obtained in step (a) is stable over time at the process temperature of 50-80° C., i.e. it does not give precipitation of the product or its chemical degradation. In particular, the solution of step (a) remained stable for more than 15 hours.

Step (b) is conducted by addition of a base to the solution of step (a). The pH of the solution during the addition of the base rises above 8. The final pH is preferably between 8 and 11, more preferably between 8.5 and 9.5. In order to maximize the recovery of the final product, it is preferable that the pH is maintained below 11.

The step (b) of the process of the present invention is carried out adding a base to the solution of the step (a).

In particular, the step (b) of the process is carried out by means an inorganic or an organic base or a mixture of these or a solution of these.

According to a preferred embodiment, the step (b) of the process according to the invention can be carried out by means a base such as an inorganic base.

The inorganic bases used to carry out the step (b) of process of the present invention can be chosen among, for example, acetates, bicarbonates, carbonates, hydroxides, phosphates, alcoholates of alkaline or alkaline-heart metals.

Said inorganic base can also be sodium hydroxide, sodium carbonate, sodium bicarbonate, potassium hydroxide, potassium carbonate, potassium bicarbonate, caesium hydroxide, caesium carbonate, lithium hydroxide, lithium carbonate, potassium dihydrogen phosphate, potassium hydrogen phosphate, potassium phosphate, sodium dihydrogen phosphate, sodium hydrogen phosphate, sodium phosphate. The sodium hydroxide, potassium hydroxide are preferred since it provides higher molar yields.

According to a more preferably embodiment, the step (b) of the process according to the invention can be carried out in the presence of sodium hydroxide, more preferable a aqueous solution of sodium hydroxide.

As the addition of a base to the solution of step (a) takes the form of a titration, it may be difficult to achieve the target pH due to the pH jump around the titration endpoint. For example, if a strong base is used, such as sodium hydroxide, it is preferable to use a diluted aqueous solution of the base. Preferably, a 10-20% aqueous solution of a strong base, more preferably sodium hydroxide, is used in step (b).

The process according to the invention can be carried out in the presence of an organic base such as, for example, an organic amine of general formula $NR_3$ with R being hydrogen or linear or branched $C_{1-7}$ alkyl and wherein the three R groups can be the same or different. The amine can also be selected among ammonia, pyrrolidine, N-alkyl substituted pirrolydine, piperidine, morpholine, N-alkyl substituted piperidine and N-alkyl substituted morpholine. Suitable bases are for instance N-Methlylmorpholine, Triethylamine, DABCO, Ethyldiisopropriliamine and TMEDA (Tetramethylethylendiamine).

Step (b) is preferably conducted at a temperature between 50° C. and 70° C., more preferably between 55° C. and 65° C. At this temperature, when the target pH is reached, a massive precipitation of Nilotinib free base occurs.

The precipitation of Nilotinib free base is maximised in step (d) by preferably decreasing the temperature of the suspension to between 30° C. and 50° C., more preferably to between 35° C. and 45° C.

Nilotinib free base is known to exist in various polymorph forms (see for example the international publication WO 2010/054056 A2 discussed in the background art). One important feature of the inventive process is that the polymorph form of Nilotinib free base raw material can be maintained in the purified material. For example, if polymorph A of Nilotinib free base raw material is used in the present process, the final Nilotinib free base product can still be a polymorph A.

However, a seeding step (c) can optionally be provided for in the process, wherein the reaction mixture is seeded with an amount of the wanted polymorph form of Nilotinib free base, in order to facilitate the precipitation of the product in the wanted form.

It has in fact been found that if, for example, the reaction vassel is contaminated by a residue of a different polymorph, e.g. polymorph B, this residual amount is able, during the process, to induce the formation of this different polymorph precipitate.

The isolation step (e) is performed by filtering, optionally washing with a solvent, preferably methanol, and drying the filtered Nilotinib free base. Drying is preferably performed under vacuum at 40° C. to 60° C., more preferably at about 45° C. to 55° C.

Purified Nilotinib free base is recovered with a molar yield above 85%, typically between 87% and 92%.

The purity of Nilotinib free base achieved by the inventive process is preferably above 99.0% (HPLC purity), more preferably above 99.80%. In particular, the detected amount of acid impurity of formula (5) is below 0.1% and the detected amount of the aniline impurity of formula (6) is below 0.03%.

The compound of formula (I), prepared according to the invention, has typically a chemical purity higher than 99.80 HPLC A/A % as determined by the method HPLC of example 9.

According to a more preferred embodiment of the process, the compound of formula (I) has chemical purity higher than 99.80 HPLC A/A % and each single impurity not more than 0.07%.

When Nilotinib free base raw material was used as polymorph A, the purified compound obtained by the inventive process showed the following analytical data:
X-ray powder diffraction pattern with characteristic peaks expressed in 2-Theta values (2θ) at: 9.0, 13.0, 13.8, 16.7, 17.8, 18.3, 19.6, 20.9, 23.9, 25.7, each peak±0.1;
melting point of 235-236° C. as measured by DSC.

According to a preferred embodiment of the present invention, the compound of formula (I) obtained in the step (e) has X-ray powder diffraction pattern with characteristic peaks expressed in 2-Theta values (2θ) at: 9.0, 13.0, 13.8, 16.7, 17.8, 18.3, 19.6, 20.9, 23.9, 25.7, each peak±0.1.

According to another preferred embodiment of the present invention, the compound of formula (I) obtained in the step (e) has melting point of 235-236° C. as measured by DSC.

In certain embodiments of the invention, the process further comprises a salification step f) of the compound obtained in step (e), of formula (I):

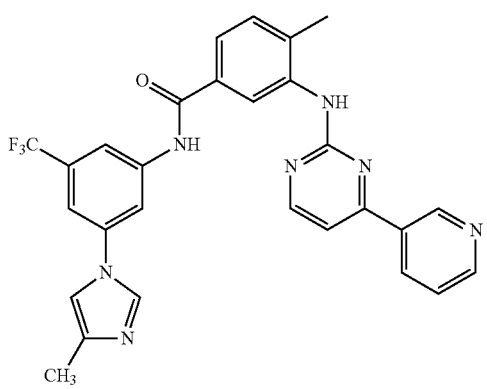

(I)

to the compound of formula (II):

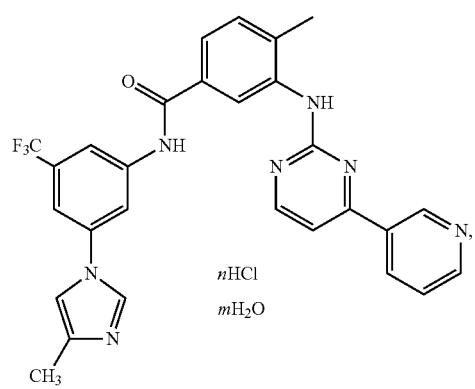

(II)

wherein n is 1 or 2 and m is 1 or 2.

Said further salification step f) can be carried out according to teachings of the skilled person regarding the salification of compound having a basic site.

In a preferred embodiment, both n and m are 1 or both n and m are 2, more preferably both n and m are 2.

According to a more preferred embodiment of the present invention, in the compound of formula (II) both n and m are 1; said compound has the following formula (II-bis):

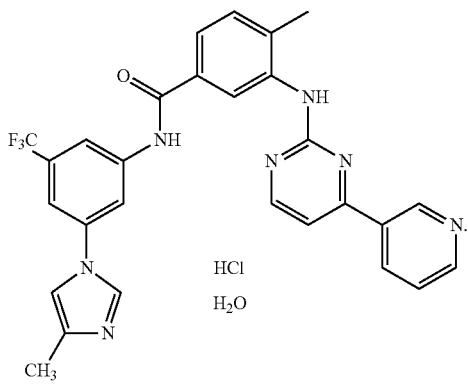

(II-bis)

According to a more preferred embodiment of the present invention, in the compound of formula (II) both n and m are 1, being Nilotinib hydrochloride hydrate.

According to a more preferred embodiment of the present invention, in the compound of formula (II) both n and m are 2; said compound has the following formula (II-tris):

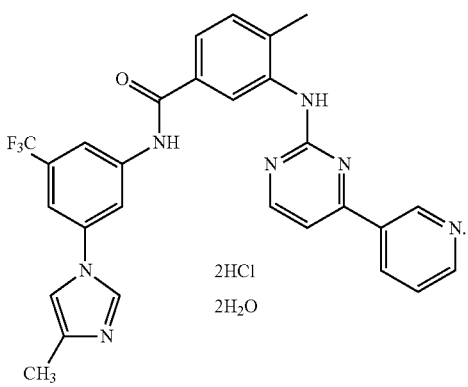

(II-tris)

According to a more preferred embodiment of the present invention, in the compound of formula (II) both n and m are 2, being Nilotinib dihydrochloride dihydrate.

The compounds of formula (II), wherein n and m are both 1 or 2, are preferred since they are those involved in the preparation of marketed active pharmaceutical ingredients (API).

The compound of formula (II) wherein both n and m are 2, prepared according to the invention, has a chemical purity higher than 99.80 HPLC A/A % as determined by the method HPLC of example 9.

According to a more preferred embodiment of the process, the compound of formula (II) wherein both n and m are 2 has chemical purity higher than 99.80 HPLC A/A % and each single impurity not more than 0.07%.

The salification step f) is preferably performed in an alcohol as a solvent. More preferably, ethanol denatured with methanol and containing about 4% v/v water is used as a solvent mixture. In certain embodiments, 15 to 25 volumes of solvent are used.

For the salification step f), the hydrochloric acid solution, e.g. a 32% hydrochloric acid solution, is preferably used in a slight excess, e.g. 5 to 10% excess, with respect to the stoichiometric amount.

In exemplary embodiments, the temperature in the salification step is initially raised to 65° C.-75° C. during the acid addition, then it is slowly cooled to about 45° C.-55° C. As the salt start to precipitate, the temperature is left to cool down to room temperature.

The recovering of the salt has been found to be a critical step. Heating under vacuum decreases the cristallinity degree of the compound. On the other hand, ethanol can hardly be eliminated by other methods such as subjecting to a stream of dry gas, e.g. dry nitrogen.

Therefore, in preferred embodiments of the invention, the salt achieved in the salification step is filtered, then it is suspended in methyl tert-butyl ether (MTBE) and stirred for some time. Finally, the solid is recovered by filtration, it is washed and then dried under a dry inert gas stream.

In certain embodiments of the invention, the process further comprises the further steps for the recovering the compound of formula (II):
 (g) suspending the salt prepared in the step f) in methyl tert-butyl ether;
 (h) stirring the obtained suspension;
 (i) recovering the solid by filtration;
 (j) drying the obtained solid under a dry inert gas stream.

All the features and preferred embodiments of the process of the present invention given above can be combined in each possible combination to carry out the claimed process.

Thus, a $C_1$-$C_4$ alcohol can be used for the purification of the compound Nilotinib of formula (I):

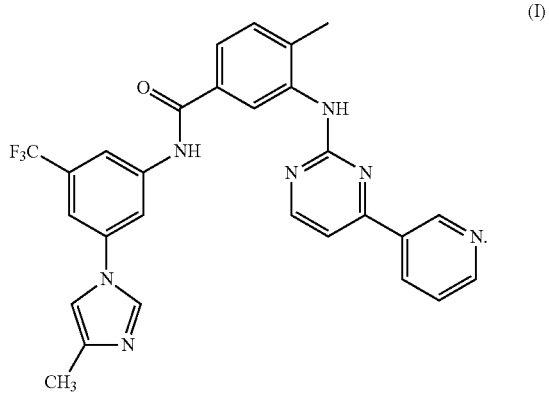 [SMILES: Cc1cn(-c2cc(NC(=O)c3ccc(C)c(Nc4nccc(-c5cccnc5)n4)c3)cc(C(F)(F)F)c2)cn1]

(I)

The term purification means to increase the chemical purity of Nilotinib and said increase can be reached by crystallization, recrystallization or precipitation of the compound of formula (I).

In a more preferred embodiment, a mixture of $C_1$-$C_4$ alcohol and a mineral acid can be used for the purification of the compound Nilotinib of formula (I):

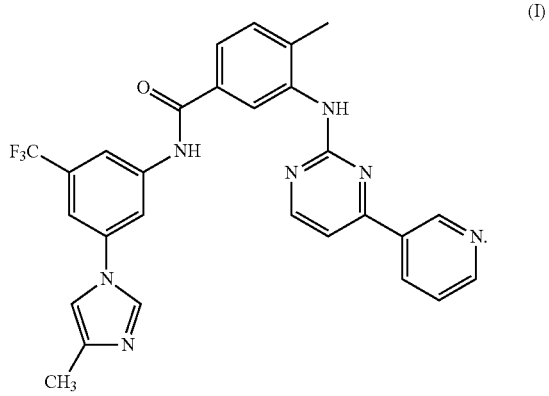 [SMILES: Cc1cn(-c2cc(NC(=O)c3ccc(C)c(Nc4nccc(-c5cccnc5)n4)c3)cc(C(F)(F)F)c2)cn1]

(I)

In a preferred embodiment, the use of a $C_1$-$C_4$ alcohol or a mixture of $C_1$-$C_4$ alcohol and a mineral acid is preferred wherein the starting compound of formula (I) is a solid.

All of the intermediates and compounds of the present invention in particular those of formula (I), (II) can be in isolated or in not isolated form, from the reaction mixture wherein they are prepared.

According to the preferred embodiment, all of the intermediates and compounds isolated are typically in form of a solid.

EXPERIMENTAL PART

Nilotinib free base and Nilotinib dihydrochloride dihydrate salt were analysed to assess their purity and their crystalline form, as well as other chemo-physical parameters.

DSC Analysis

DSC testing was performed in a sealed medium pressure stainless steel crucible. All the testing was performed by heating the sample from 30° C. at a rate of 10° C./minute up to a maximum temperature of 280° C.

An isothermal analysis of reaction mixture was also performed in order to check stability near process temperature.

A sample of 3.5200 mg of Nilotinib salt was weighed into a 40 μL aluminium crucible with a pinhole lid and heated from 25 to 300° C. at a rate of 10° C./min, under nitrogen (50 mL/min).

Thermal events between about 241° C. and about 248° C. were recorded.

Hygroscopicity of Nilotinib Salt

The hygroscopicity of the Nilotinib dihydrochloride dihydrate was determined by DVS (Dynamic Vapour Sorption) with a Q5000 TA instrument. This is a gravimetric technique that measures how much water is absorbed or desorbed by a sample at different relative humidities (RH). At each RH level, the sample mass must be allowed to reach gravimetric equilibrium (or surpass the time limit) before progressing to the next humidity level. Sorption and desorption isotherms were performed at 25° C. over a range of 0-95% RH.

The sample was not previously dried but it was exposed to 0% RH until a stable weight was reached before starting the DVS cycle. This equilibration step allows the elimination of the possible adsorbed humidity. DVS analysis was performed with 9.8745 mg of Nilotinib-dihydrochloride dihydrate according to the following conditions: Equilibration at 25° C. under 0% RH; Increase to the higher RH % level when the weigh variation of the sample is inferior to 0.02% after 10 min or after a time limit of 300 min.

This analysis showed that between 25 and 85% RH, the increase of water uptake is moderate (+1.6% w/w) and then increases to 2.4% w/w at 95% RH.

Synchrotron X-Ray Powder Diffraction Analysis

The powder of each sample was introduced in a 1.5 mm glass capillary and then the open end was sealed with a flame and covered with sealing wax.

The diffraction measurements were performed at room temperature at the ALBA synchrotron. Data were collected in transmission geometry using radiation at 20 keV, λ=0.61937+/−0.00002 Å, by means of a high throughput Mython detector. Samples were allowed to rotate during the experiments.

This experiments conducted on Nilotinib dihydrochloride dihydrate gave the following characteristic peaks expressed in 2-Theta values (2θ): 9.0, 13.0, 13.8, 16.7, 17.8, 18.3, 19.6, 20.9, 23.9, 25.7, each peak±0.1.

The starting material compound (IV) and (V), are reactants largely commercially available, for example, for supplied by: Toronto Research Chemicals Product List, ABCR GmbH Product List, Activate Scientific.

The seeding of Nilotinib base form A can be prepared according the teaching of international application publication No. WO 2007/015870 in the example 30 at page. 37.

Example 1: Standard Synthesis of the Compound of Formula (I)

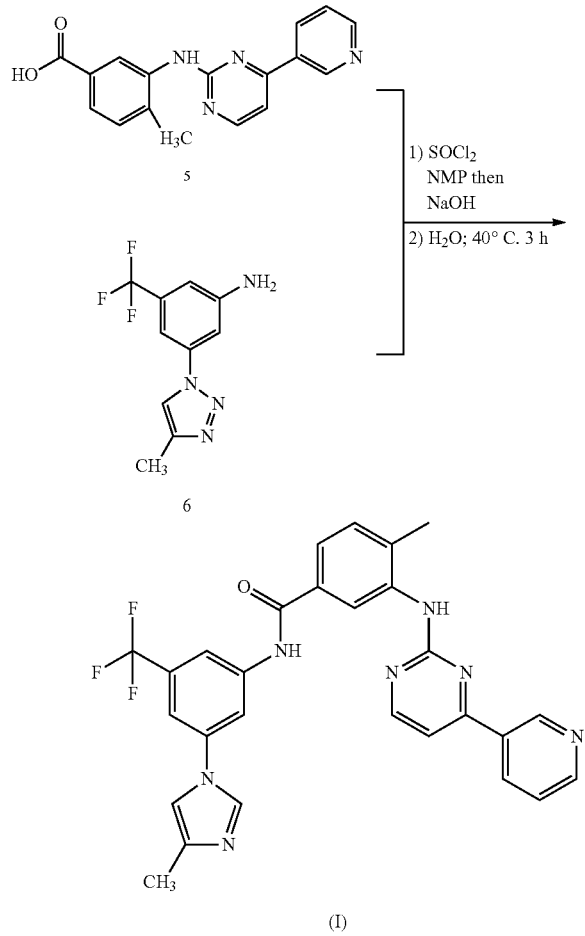

Example 2: Synthesis of the Compound of Formula (I)

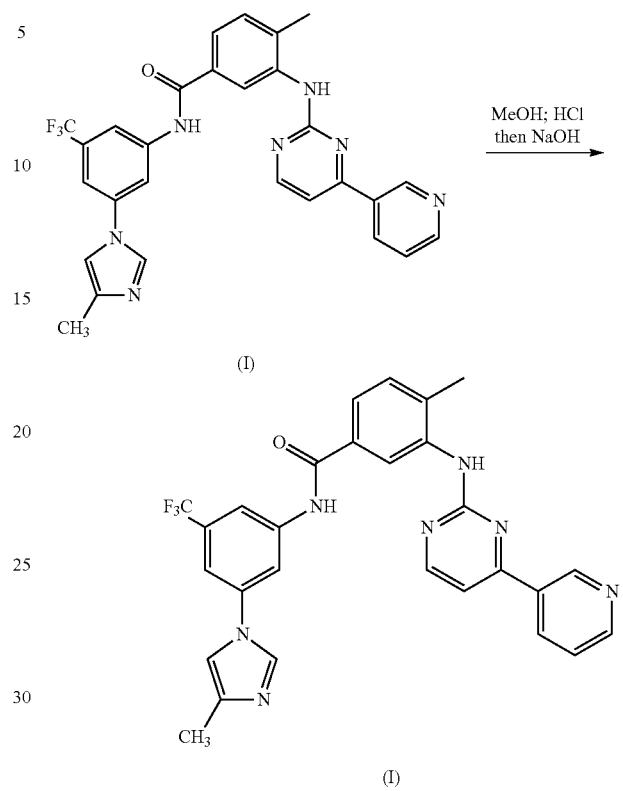

To a mixture of compound (I) (800 g, 1.51 mol) in methanol (12000 mL) was added a aqueous solution of hydrochloric acid 32% until the pH was 2.5-3.5 (indicative quantity 148 mL). Then the obtained mixture was heated at 60-65° C. and was stirred at the same temperature for 1 hour, until completely dissolution. Then to the obtained solution was added a aqueous solution of sodium hydroxide 15% until the pH 9 (indicative quantity 307 mL). Then the obtained mixture was cooled in 1 hour to T=40° C. and then was filtered at the same temperature. The obtained filtrate containing the compound (I) was washed with methanol (800 mL). The obtained solid was dried on vacuum to give compound (I) (738.4 g, 92% yield, HPLC purity 99.7%, acid (IV) impurity <0.05%) as a white solid.

Example 3: Synthesis of the Compound of Formula (I)

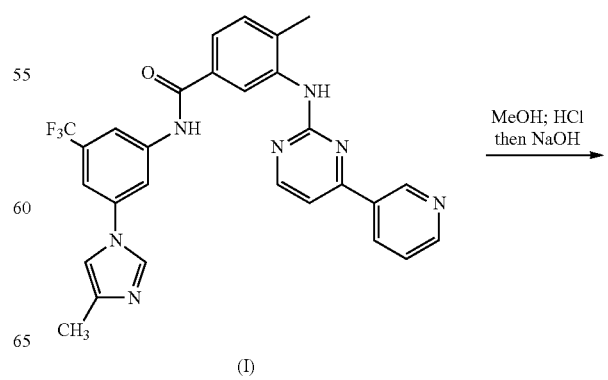

A mixture of compound 5 (530 g, 1.73 mol) in N-methyl-2-pyrrolidone (abbreviated NMP) (3710 mL) was heated at 60° C. and then was added, in around 30 min., thionyl chloride (159 g, 1.34 mol). Then the reaction was stirred at the same temperature for 1 hour. Then to the reaction mixture was added a solution of compound 6 (417.3 g, 1.73 mol) in NMP (1590 mL). The obtained reaction mixture was heated at 90° C. and the reaction was stirred at the same temperature for 2 hours. Then the reaction mixture was cooled to 80° C. and water (4770 mL) was added. The pH was adjusted to pH=11 with sodium hydroxide solution 30% (988.6 mL). Then the obtained mixture was cooled to T=40° C. and stirred for 3 hours. Then the mixture was filtered and the filtrate containing the compound (I) was washed with water. The obtained solid was dried on vacuum to give compound (I) (824.6 g, 86% yield, HPLC purity 99.5%, acid (IV) impurity 0.1%) as a white solid.

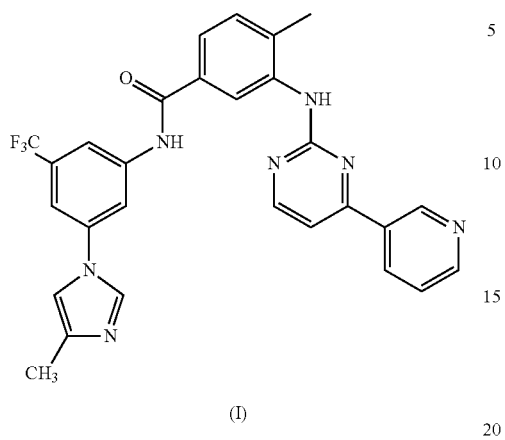

(I)

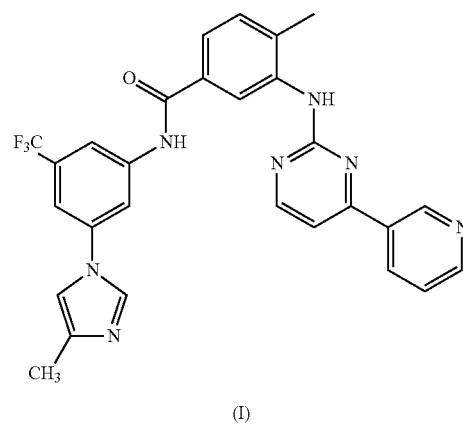

(I)

To a mixture of compound (I) (10 g, 18.88 mmol), acid 5 (1 g, 3.26 mmol) and aniline 6 (1 g, 4.156 mmol) in methanol (150 mL) was added a aqueous solution of hydrochloric acid 32% until the pH was 2.5-3.5 (indicative quantity 1.8 mL). Then the obtained mixture was heated at 60-65° C. and was stirred at the same temperature for 1 hour, until completely dissolution. Then to the obtained solution was added a aqueous solution of sodium hydroxide 30% until the pH 9 (indicative quantity 2.1 mL). Then the obtained mixture was cooled in 1 hour to T=40° C. and then was filtered at the same temperature. The obtained filtrate containing the compound (I) was washed with methanol (10 mL). The obtained solid was dried on vacuum to give compound (I) (8.89 g, 89.9% yield, HPLC purity 99.90%, acid 5 impurity 0.02% and aniline 6 impurity 0.00%, as a white solid.

Example 4: Synthesis of the Compound of Formula (I)

To a mixture of compound (I) (10 g, 18.88 mmol) in methanol (150 mL) was added a aqueous solution of hydrochloric acid 32% until the pH was 3.0-3.5 (indicative quantity 1.7 mL, i.e. 0.9 eq.). Then the obtained mixture was heated at 60-65° C. and was stirred at the same temperature for 1 hour, until completely dissolution. Then to the obtained solution was added a aqueous solution of sodium hydroxide 30% until the pH 9.0-9.5 (indicative quantity 1.9 mL). Then the obtained mixture was cooled in 1 hour to T=40° C. and then was filtered at the same temperature. The obtained filtrate containing the compound (I) was washed with methanol (10 mL). The obtained solid was dried on vacuum to give compound (I) (8.20 g, 82% yield, HPLC purity 99.69%, acid 5 impurity 0.07% and aniline 6 impurity 0.00%, as a white solid.

Example 5: Synthesis of the Compound of Formula (I)

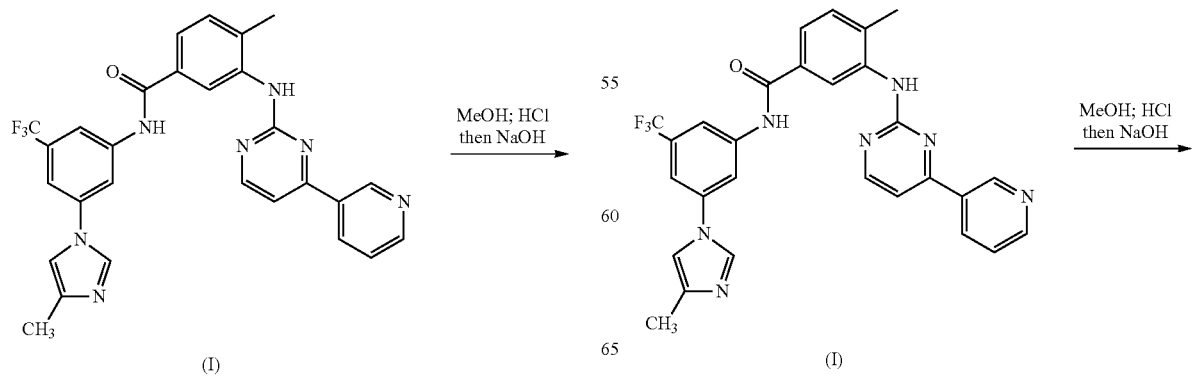

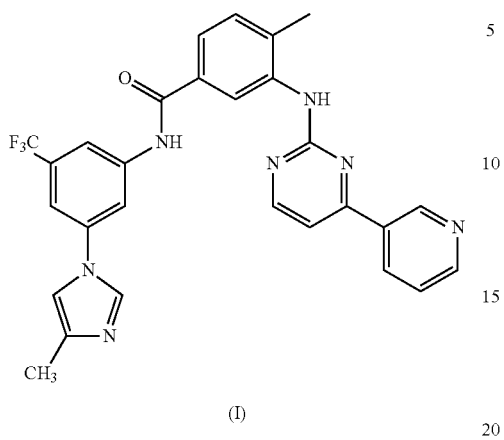

(I)

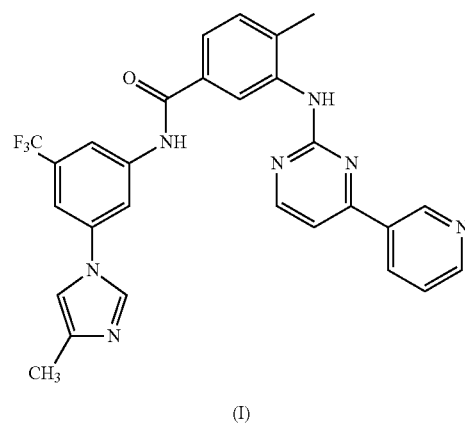

(I)

To a mixture of compound (I) (10 g, 18.88 mmol) in methanol (150 mL) was added 2.0 mL of a aqueous solution of hydrochloric acid 32% (i.e. 1.1 eq.). Then the obtained mixture was heated at 60-65° C. and was stirred at the same temperature for 1 hour, until completely dissolution. Then to the obtained solution was added a aqueous solution of sodium hydroxide 30% until the pH 9.0-9.5 (indicative quantity 2.0 mL). Then the obtained mixture was cooled in 1 hour to T=40° C. and then was filtered at the same temperature. The obtained filtrate containing the compound (I) was washed with methanol (10 mL). The obtained solid was dried on vacuum to give compound (I) (8.30 g, 83% yield, HPLC purity 99.86%, acid 5 impurity 0.04% and aniline 6 impurity 0.00%, as a white solid.

To a mixture of compound (I) (10 g, 18.88 mmol) in methanol (150 mL) was added a aqueous solution of hydrochloric acid 32% until the pH was 3.0-3.5 (indicative quantity 1.8 mL). Then the obtained mixture was heated at 60-65° C. and was stirred at the same temperature for 1 hour, until completely dissolution. Then to the obtained solution was added a aqueous solution of sodium hydroxide 30% until the pH 8 (indicative quantity 2.0 mL). Then the obtained mixture was cooled in 1 hour to T=40° C. and then was filtered at the same temperature. The obtained filtrate containing the compound (I) was washed with methanol (10 mL). The obtained solid was dried on vacuum to give compound (I) (8.69 g, 87% yield, HPLC purity 99.92%, acid (IV) impurity 0.07%, as a white solid.

Example 6: Synthesis of the Compound of Formula (I)

Example 7: Synthesis of the Compound of Formula (I)

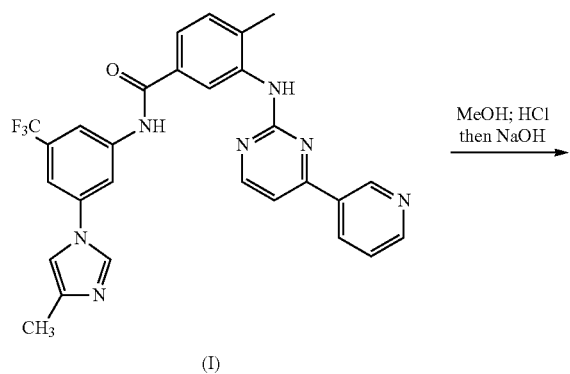

(I)  $\xrightarrow{\text{MeOH; HCl then NaOH}}$

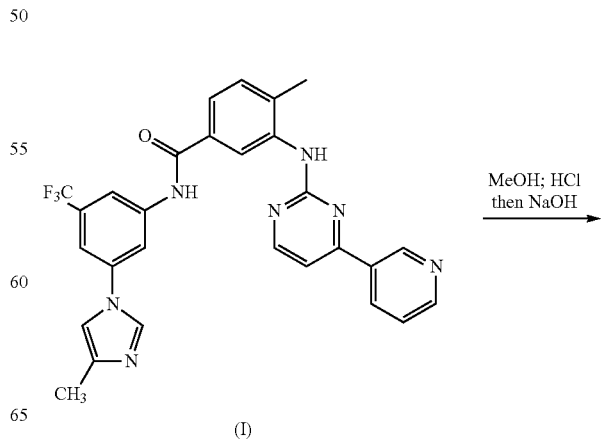

(I)  $\xrightarrow{\text{MeOH; HCl then NaOH}}$

-continued

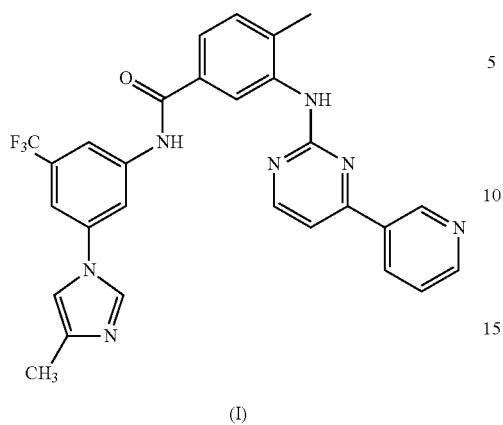

(I)

To a mixture of compound (I) (10 g, 18.88 mmol) in methanol (150 mL) was added a aqueous solution of hydrochloric acid 32% until the pH was 3.0-3.5 (indicative quantity 1.8 mL). Then the obtained mixture was heated at 60-65° C. and was stirred at the same temperature for 1 hour, until completely dissolution. Then to the obtained solution was added a aqueous solution of sodium hydroxide 30% until the pH 10 (indicative quantity 2.1 mL). Then the obtained mixture was cooled in 1 hour to T=40° C. and then was filtered at the same temperature. The obtained filtrate containing the compound (I) was washed with methanol (10 mL). The obtained solid was dried on vacuum to give compound (I) (8.85 g, 88.5% yield, HPLC purity 99.93%, acid (IV) impurity 0.05%, as a white solid.

Example 8: Synthesis of the Compound of Formula (II) in which n and m are Both 2 (Compound of Formula (II-Tris))

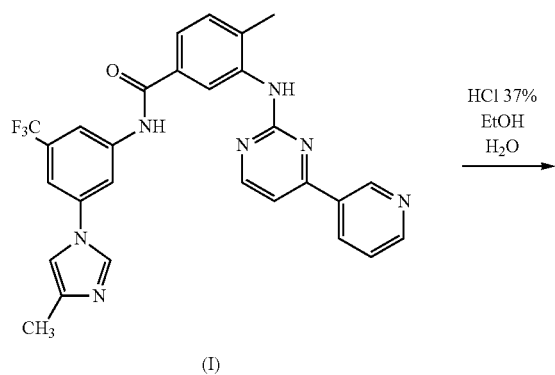

-continued

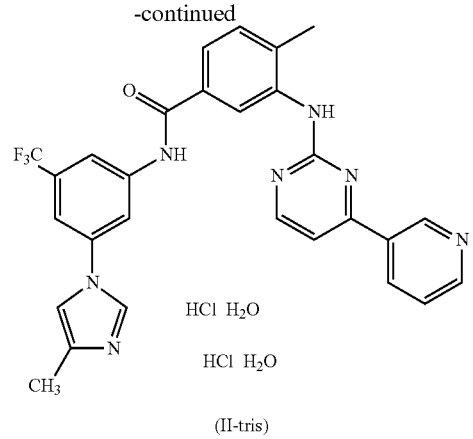

(II-tris)

To a suspension of compound (I) (500 g, 0.944 mol) in ethanol (9600 mL) and water (400 mL) was heated at 70° C. and then was added, in around 20 min., a aqueous solution of hydrochloric acid 32% (189 mL). Then the obtained mixture was stirred at 70° C. for 30 minutes. Then the obtained mixture was cooled in 1 hour to T=50° C. and was stirred at the same temperature for 2.5 hours. Then the mixture was cooled in room temperature and was stirred at the same temperature for 15 hours. Then the obtained suspension was filtered and the obtained filtrate was washed twice with methyl-tertbutyl ether (2×500 mL). The obtained wet solid was suspended in methyl-tertbutyl ether (6000 mL) and the obtained suspension was stirred for 1 hour. Then the obtained suspension was filtered under nitrogen stream and the obtained filtrate was washed three times with methyl-tertbutyl ether (3×500 mL). The obtained solid was dried by dry nitrogen stream to give compound (II-tris) which is Nilotinib dihydrochloride dihydrate (542.56 g, 90% yield, HPLC purity 99.95%) as a pale yellow solid.

Example 9: Analytic Method for Determining the Chemical Purity and the Amount of Impurities of the Present Invention The method monitoring the reaction of example from 1 to 8 and the purity of the compound of formula (I) and formula (II), via HPLC:
Column: Waters XSelect CSH C18 Column, 130 Å, 3.5 μm, 4.6 mm×150 mm;
Temp. Column: 40° C.;
Mobile Phase A: Phosphate buffer (Transfer 1.31 g of $KH_2PO_4$, accurately weighed, in 1000 mL volumetric flask, add 500 mL of Water milliQ and well mix. Add 26.7 μL of $H_3PO_4$ 85%, accurately measured, and bring to volume; Filter the solution trough a 0.22 μm Millipore filter then degas; Check the pH; the pH should be approximately 3.65±0.05, If the pH is not between 3.60 and 3.70, adjust the pH with 85% Phosphoric Acid until it is between 3.60 and 3.70);
Mobile Phase B: Acetonitrile;
Gradient

| Time (min) | % A | % B |
|---|---|---|
| 0 | 90 | 10 |
| 10 | 55 | 45 |
| 20 | 30 | 70 |
| 30 | 30 | 70 |

-continued

| Time (min) | % A | % B |
|---|---|---|
| 30.1 | 90 | 10 |
| 35 | 90 | 10 |

Flow: 1.0 mL/min;
UV Detector: 260 nm;
Injection Volume: 5 μL;
Analysis Time: 35 min;
Diluent: $H_3PO_4$ 0.1%/Methanol 1/9.

The invention claimed is:
1. A process of purifying a compound of formula (I):

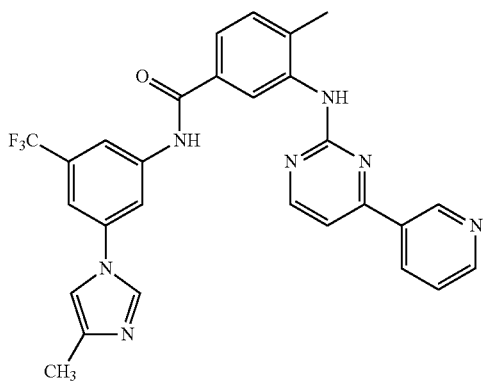

(I)

comprising the following steps:
(a) providing a solution comprising a free base raw material of the compound of formula (I):
and a mixture of a $C_1$-$C_4$ alcohol and a mineral acid, wherein the raw material comprises from about 0.1% to about 8% of a compound of formula (V)

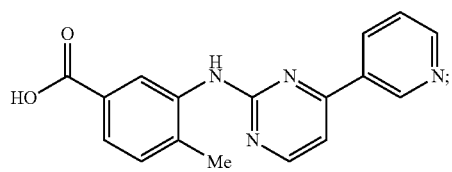

(V)

(b) adding a base to the solution of step (a) to achieve a value of pH of more than 8;
(c) obtaining a suspension of the compound of formula (I);
(d) isolating the compound of formula (I), wherein the compound of formula (I) comprises less than 0.07% of the compound of formula (V).

2. The process according to claim 1, wherein step (a) comprises the following steps:
(a-1) providing the free raw base of the compound of formula (I) as a solid; and
(a-2) dissolving said solid in a mixture of a $C_1$-$C_4$ alcohol and a mineral acid.

3. The process according to claim, wherein one or more of steps (a), (b), or (c) is carried out at a temperature of between 50° C. and 80° C.
4. The process according to claim, wherein step (a) is carried out at a pH of between 2 and 4.
5. The process according to claim 1, wherein the mineral acid in 1 step (a) is an aqueous mineral acid.
6. The process according to claim 5, wherein the mineral acid in step (a) is aqueous hydrochloric acid.
7. The process according to claim 1, wherein the $C_1$-$C_4$ alcohol is methanol.
8. The process according to claim 1, wherein the solution of step (a) comprises from 10 to 20 volumes of $C_1$-$C_4$ alcohol.
9. The process according to claim 1, wherein step (b) is carried out at a pH of between 8.5 and 9.5.
10. The process according to claim 1, wherein the compound of formula (I) obtained in step (d) has X-ray powder diffraction pattern with characteristic peaks expressed in 2-Theta values (2θ) at: 9.0±0.1, 13.0±0.1, 13.8±0.1, 16.7±0.1, 17.8±0.1, 18.3±0.1, 19.6±0.1, 20.9±0.1, 23.9±0.1, and 25.7±0.1.
11. The process according to claim 1, further comprising salification step (e) of the compound obtained in step (d) to a compound of formula (II):

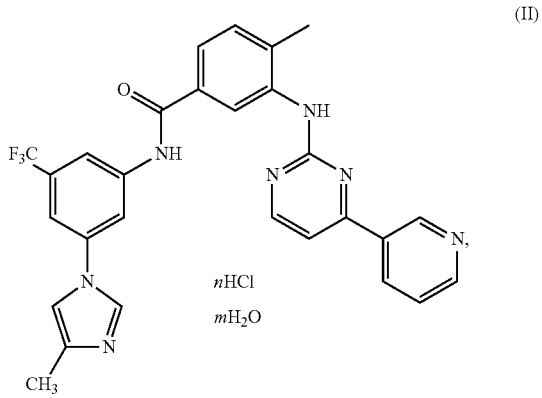

(II)

wherein n is 1 or 2 and m is 1 or 2.
12. The process according to claim 11, wherein n=m=1 or 2.
13. The process according to claim 11, further comprising the following steps:
(f) suspending the salt prepared in the step (e) in methyl tert-butyl ether;
(g) stirring the obtained suspension;
(h) recovering the solid by filtration; and
(i) drying the obtained solid under a dry inert gas stream.
14. The process according to claim 1, further comprising a step of seeding the solution of step (b).
15. The process according to claim 1, wherein the mineral acid is chosen from hydrochloric acid, hydrobromic acid, hydroiodic acid, sulfuric acid, or nitric acid.
16. The process according to claim 1, wherein the $C_1$-$C_4$ alcohol is chosen from methanol, ethanol, n-propanol, isopropanol, n-butanol, isobutanol, sec-butanol or tert-butanol.

* * * * *